(12) United States Patent
Han et al.

(10) Patent No.: US 10,351,885 B2
(45) Date of Patent: Jul. 16, 2019

(54) VARIANT MICROORGANISM PRODUCING 5-AMINOLEVULINIC ACID AND METHOD FOR PREPARING 5-AMINOLEVULINIC ACID USING THEROF

(71) Applicant: KOREA UNIVERSITY RESEARCH AND BUSINESS FOUNDATION, Seoul (KR)

(72) Inventors: Sung Ok Han, Seoul (KR); Seung-Kyou You, Jeollabuk-do (KR); Jeong-Eun Hyeon, Seoul (KR); Young-jin Ko, Gangwon-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 15/218,029

(22) Filed: Jul. 24, 2016

(65) Prior Publication Data
US 2017/0292134 A1  Oct. 12, 2017

(30) Foreign Application Priority Data
Apr. 8, 2016 (KR) .................. 10-2016-0043287

(51) Int. Cl.
C12P 13/00 (2006.01)
C12N 9/02 (2006.01)
C12N 9/90 (2006.01)
C12N 1/20 (2006.01)

(52) U.S. Cl.
CPC .............. *C12P 13/001* (2013.01); *C12N 1/20* (2013.01); *C12N 9/0008* (2013.01); *C12N 9/90* (2013.01); *C12Y 102/0107* (2013.01); *C12Y 504/03008* (2013.01)

(58) Field of Classification Search
None
See application file for complete search history.

(56) References Cited

U.S. PATENT DOCUMENTS 3,511,752 A * 5/1970 Kimura .................. C12P 13/14
435/110

OTHER PUBLICATIONS

Li et al., FEMS Microbiol. Lett. 350:209-215, 2014 (Year: 2014).*
Kang et al., Met. Engineer. 13:492-498, 2011 (Year: 2011).*
UniProt Database Accession No. A9MPA0, Jan. 2015, 2 pages (Year: 2015).*
UniProt Database Accession No. P0A1Q6, Dec. 2015, 3 pages (Year: 2015).*
Merriam-Webster online dictionary definition of "represent", 1 page, last viewed on Jan. 11, 2018 (Year: 2018).*
Xie, L., "Metabolic Engineering for 5-Aminolevulinic Acid Production by *Escherichia coli* Carrying Rhodobacter spaeroides HemA", Thesis, University of Georgia, 2002 (Year: 2002).*
Tavakkoli et al., Food Bioprocess. Technol. 5:92-99, 2012 (Year: 2012).*
Bailey, J., "Toward a science of metabolic engineering", Science 252:1668-1675, 1991 (Year: 1991).*
Kawahara et al., "Relationship between the Glutamate Production and the Activity of 2-Oxoglutarate Dehydrogenase in Brevibacterium lactofermentum", Biosci. Biotechnol. Biochem. 61:1109-1112, 1997 (Year: 1997).*
Beale, S., et al., "The Biosynthesis of delta-Aminolevulinic Acid in Higher Plants: II. Formation of C-delta-Aminolevulinic Acid from Labeled Precursors in Greening Plant Tissues", "Plant Physiol.", Feb. 1974, pp. 297-303, vol. 53, No. 2.
Beale, S., et al., "Chemical Synthesis of 4,5-Dioxovaleric Acid and its Nonenzymatic Transamination to 5-Aminolevulinic Acid", "Phytochemistry", 1979, pp. 441-444, vol. 18.
Hua, Z., et al., "Effectiveness of delta-Aminolevulinic Acid-induced Protoporphyrin as a Photosensitizer for Photodynamic Therapy in Vivo", "Cancer Research", Apr. 15, 1995, pp. 1723-1731, vol. 55, No. 8.
Hyeon, J., et al., "Production of minicellulosomes for the enhanced hydrolysis of cellulosic substrates by recombinant Corynebacterium glutamicum", "Enzyme and Microbial Technology", Apr. 7, 2011, pp. 371-377, vol. 48, No. 4-5.
Jaenchen, R., et al., "Inhibition of factor F430 synthesis by levulinic acid in Methanobacterium thermoautotrophicum", "FEMS Microbiology Letters", 1981, pp. 167-170, vol. 12.
Kipe-Nolt, J., et al., "Biosynthesis of delta-Aminolevulinic Acid from Glutamate in Agmenellum quadruplicatum", "Plant Physiol.", Jan. 1980, pp. 126-128, vol. 65, No. 1.
Matsumoto, H., et al., "Porphyrin Intermediate Involved in Herbicidal Action of Delta-Aminolevulinic Acid on Duckweed (*Lemna paucicostata hegelm.*)", "Pesticide Biochemistry and Physiology", Jan. 13, 1994, pp. 214-221, vol. 48.
Neumann, E., et al., "Gene transfer into mouse lyoma cells by electroporation in high electric fields", "The EMBO Journal", 1982, pp. 841-845, vol. 1, No. 7.
Ramzi, A., et al., "5-Aminolevulinic acid production in engineered Corynebacterium glutamicum via C5 biosynthesis pathway", "Enzyme and Microbial Technology", Dec. 2015, pp. 1-7, vol. 81, No. 1-7.
Rebeiz, C., et al., "Photodynamic herbicides: 1. Concept and phenomenology", "Enzyme Microb. Technol.", Sep. 1984, pp. 390-401, vol. 6.

(Continued)

*Primary Examiner* — David Steadman
(74) *Attorney, Agent, or Firm* — Hultquist, PLLC; Steven J. Hultquist

(57) ABSTRACT

The present invention relates to a mutant microorganism having the ability to produce 5-aminolevulinic acid, and more particularly, to a mutant microorganism having the ability to produce 5-aminolevulinic acid wherein a glutamyl-tRNA reductase-encoding gene is introduced in a glutamic acid-producing microorganism, and to a method for producing 5-aminolevulinic acid using the same. According to the present invention, 5-aminolevulinic acid that is useful in the medical or agricultural field can be produced in a significantly higher yield than that of conventional production methods.

2 Claims, 4 Drawing Sheets

Specification includes a Sequence Listing.

(56) References Cited

OTHER PUBLICATIONS

Rebeiz, N., et al., "Photodestruction of tumor cells by induction of endogenous accumulation of protoporphyrin IX: enhancement by 1,10-phenanthroline", "Photochemistry and Photobiology", Mar. 1992, pp. 431-435, vol. 55, No. 3.

Sasaki, K., et al., "Production of 5-Aminolevulinic Acid by Photosynthetic Bacteria", "J. Ferment. Technol.", Apr. 14, 1987, pp. 511-515, vol. 65, No. 5.

Sasaki, K., et al., "Effect of Culutre pH on the Extracellular Production of 5-Aminolevulinic Acid by Rhodobacter sphaeroides from Volatile Fatty Acids", "Biotechnology Letters", , pp. 859-864, vol. 15, No. 8, 1993.

Tanaka, T., et al., "5-aminolevulenic acid rhodobacter sphaeroides", "Biotechnology Letters", 1991, pp. 589-594, vol. 13, No. 8.

Matsumoto, T.H., et al., "Structural Activity Correlation of the Growth Inhibitory Substance Rhafnananin", "Journal of Weed Science and Technology", 1992, p. 60, vol. 37.

Matsumoto, T.H., et al., "Structural Activity Correlation of the Growth Inhibitory Substance Rhafnananin", "Journal of Weed Science and Technology", 1992, p. 60, vol. 37 (Machine Translation).

Shiio, I., et al., "Cellular Permeability and Extracellular Formation of Glutamic Acid in Brevibacterium flavum", "The Journal of Biochemistry", 1963, pp. 333-340, vol. 53, No. 5.

Wang, L., et al., "A Mutant HemA Protein with Positive Charge Close to the N Terminus is Stabilized against Heme-Regulated Proteolysis in *Salmonella typhimurium*", "Journal of Bacteriology", Oct. 1999, pp. 6033-6041, vol. 181, No. 19.

Yu, X., et al., "Engineering Corynebacterium Glutamicum to Produce 5-aminolevulinic Acid from Glucose", "Microbial Cell Factories", 2015, pp. 1-10, vol. 14, No. 183.

Becker, M., et al., "Glutamate efflux mediated by Corynebacterium MscCG, *Escherichia coli* MscS, and their derivatives", "Biochimica et Biophysica Acta", 2013, pp. 1230-1240, vol. 1828, Publisher: Elsevier.

Schultz, C., et al., "Glutamate production by Corynebacterium glutamicum: dependence on the oxoglutarate dehydrogenase inhibitor protein Odhl and protein kinase PknG", "Applied Microbial and Cell Physiology", 2007, pp. 691-700, vol. 76, Publisher: Springer.

\* cited by examiner

VARIANT MICROORGANISM PRODUCING 5-AMINOLEVULINIC ACID AND METHOD FOR PREPARING 5-AMINOLEVULINIC ACID USING THEROF

CROSS-REFERENCE TO RELATED APPLICATION

The priority of Korean Patent Application No. 10-2016-0043287 filed Apr. 8, 2016 is hereby claimed under the provisions of 35 USC 119. The disclosure of Korean Patent Application No. 10-2016-0043287 is hereby incorporated herein by reference in its entirety, for all purposes.

TECHNICAL FIELD

The present invention relates to a mutant microorganism having the ability to produce 5-aminolevulinic acid, and more particularly, to a mutant microorganism having the ability to produce 5-aminolevulinic acid wherein a gene encoding glutamyl-tRNA reductase is introduced in a glutamic acid-producing microorganism, and to a method for producing 5-aminolevulinic acid using the same.

BACKGROUND ART

Generally, 5-aminolevulinic acid (ALA) is a major precursor of tetrapyrrole compounds such as heme, bacteriochlorophylls, corrinoid and the like in all organisms, and is a photodynamic compound that forms Pchlide, a strong oxidant, by sunlight. The Pchlide induces a series of oxidation reactions that selectively destroy phospholipids in the leaves of dicotyledonous plants to kill the plants. Thus, ALA can be used as an environmentally friendly herbicide that selectively kills weeds without causing damage to humans, animals and agricultural crops (see Rebeiz C. A. et al., *Enzyme Microb. Technol.,* 6:390, 1984).

In addition to this use of ALA as herbicide, ALA has the effect of promoting plant growth by stimulating plant photosynthesis, inhibiting breathing and promoting carbon dioxide assimilation, when it is used at low concentrations (Hua Z., et al., *Cancer Reasearch.* 55:1723, 1995); Matsumoto T. H., et al., *Weed Research,* 37:60, 1992); Matsumoto T. H., et al., *Pesticide Biochemistry,* 48:214, 1994; Rebeiz N., et al., *Photochem. Photobiol.,* 55:431, 1995). It was found that, when rice seeds were immersed in 1-3 ppm of an ALA solution for 1-48 hours and then sowed, the size and weight of the plant increased and the root growth of the plant was promoted.

In addition, ALA can also be used as an insecticide against noxious insects such as *Trichopusia ni*. In particular, regarding the insecticidal effect of ALA, the stage of action of ALA is very complicated, unlike conventional insecticides that are involved in a certain metabolic stage to exhibit their effect, and thus it is difficult for noxious insects to develop resistance to ALA, indicating that ALA can be used as an environmentally friendly insecticide. Furthermore, it was reported that ALA can be used as biologically active substances (such as skin cancer treating agents and antimicrobial drugs) in the medical field. Particularly, it was found that ALA can also be widely used as a photosensitizer in photodynamic therapy (PDP) for treating a variety of malignant tumors. Thus, studies on ALA have been actively conducted. Particularly, it was found that, when ALA was administered to a malignant tumor site, it rapidly increased the intracellular concentration of porphyrin, particularly protoporphyrin IX that is the final precursor in the heme biosynthesis pathway, and thus the tumor was damaged and killed by irradiation with visible light. However, it was found that, because normal cells absorb ALA at a slow rate and grow at a slow rate, compared to those of tumor cells, the concentration of protoporphyrin IX that is accumulated in normal cells is relatively low, and thus damage to normal cells by light irradiation is low.

Currently, ALA is produced using complicated organic synthesis processes (Beale S. I., et al., *Phytochemistry,* 18:441, 1979), but is not commercially profitable due to its high production cost. For this reason, studies have been conducted on ALA production methods based on fermentation of microorganisms, including *Rhodobacter sphaeroides, Clostridium thermoaceticum, Methanobacterium thermoautotropicum, Agnemellum guadruplicum, Anacystis marina,* and *Chlorella vulgaris,* and on the use thereof (Sasaki K., et al., *J. Ferment. Technol.,* 65:511, 1987; Sasaki K., et al., *Biotechnol. Lett.,* 15:859, 1993; Tanaka T., et al., *Biotechnol. Lett.,* 13:589, 1991; Janschen R., et al., *FEMS Microb. Lett.,* 12:167, 1981; Kipe-Not J. A. and Steven S. E., *Plant Physiol.,* 65:126, 1980; Beale S. I. and Castelfranco P. A., *Plant Physiol.,* 53:297, 1974).

It is known that ALA, a precursor of heme, is biosynthesized by two biosynthetic systems (C4 and C5 pathways). ALA by the C4 pathway, which is found in animals, fungi, bacteria, etc., is produced through the condensation of glycine and succinyl-CoA, and this condensation reaction is catalyzed by ALA synthase that is a pyridoxal phosphate-dependent enzyme. In addition, the C5 pathway is found in plants, algae, *E. coli*, etc.

The molecular biological ALA biosynthetic pathway was identified by isolation of ALA auxotrophs. It was found that ALA synthase genes in the C4 pathway are two isozymes (hemA and hemi), whereas the C5 pathway is composed of hemA, hemL and hemM genes.

In an attempt to increase the synthesis of ALA by microorganisms, both the supplement of precursors (glutamic acid, glycine and succinic acid) into culture media and studies on the isolation of lower fatty acids from organic waste resources and the effect of addition thereof were reported. In addition, studies on the increase in ALA production by pH and temperature control, oxygen supply, light irradiation for photosynthetic bacteria, etc., were also reported.

The present inventors have made extensive efforts to develop an efficient method capable of producing a large amount of 5-aminolevulinic acid, and as a result, have found that, when genes capable of producing 5-aminolevulinic acid are introduced into a microorganism that produces glutamic acid from the 5-carbon metabolic pathway among microbial metabolic pathways, the resulting microorganism is capable of producing 5-aminolevulinic acid in a high yield, thereby completing the present invention.

DISCLOSURE OF INVENTION

Technical Problem

It is an object of the present invention to provide a mutant microorganism capable of producing 5-aminolevulinic acid in a high yield.

Another object of the present invention is to provide a method for producing 5-aminolevulinic acid using the above-described mutant microorganism.

Still another object of the present invention is to provide a method for producing the above-described mutant microorganism.

Other features, embodiments, aspects, objects, and advantages of the invention will be more fully apparent from the ensuing disclosure and claims.

Technical Solution

To achieve the above object, the present invention provides a mutant microorganism having the ability to produce 5-aminolevulinic acid wherein a gene encoding mutant glutamyl tRNA reductase is introduced in a glutamic acid producing-microorganism; and wherein the mutant glutamyl tRNA reductase has two lysine additions at 3rd position of an amino acid sequence selected from the group consisting of SEQ ID NO 6, SEQ ID NO 7, SEQ ID NO 8, SEQ ID NO 9, and SEQ ID NO 10.

The present invention also provides a method for producing 5-aminolevulinic acid, comprising the steps of: (a) culturing in a glucose-containing medium the above-described mutant microorganism having the ability to produce 5-aminolevulinic acid, thereby producing 5-aminolevulinic acid; and (b) recovering the produced 5-aminolevulinic acid.

The present invention also provides a method for producing a mutant microorganism having the ability to produce 5-aminolevulinic acid, the method comprising introducing a gene encoding glutamyl-tRNA reductase into a glutamic acid-producing microorganism.

The present invention further resides in various aspects, embodiments, and implementations, as hereinafter more fully described.

Advantageous Effects

According to the present invention, 5-aminolevulinic acid that is useful in the medical or agricultural field can be produced in a significantly higher yield than that of conventional production methods.

BEST MODE FOR CARRYING OUT THE INVENTION

Figure 1:
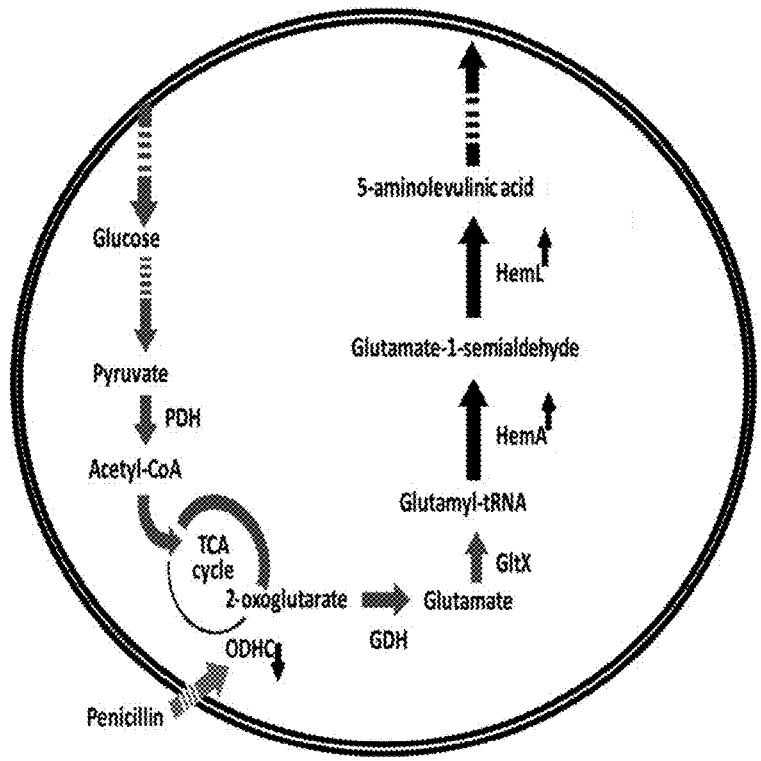
FIG. 1 schematically shows a metabolic engineering strategy for biosynthesizing 5-aminolevulinic acid in *Corynebacterium glutamicum*.

In the present invention, in order to produce a mutant microorganism having an enhanced ability to produce 5-aminolevulinic acid, a mutant microorganism having introduced therein a HemA gene encoding glutamyl-tRNA reductase was produced for the purpose of producing 5-aminolevulinic acid using the C5 pathway of *Corynebacterium glutamicum* that is an industrial strain. It was found that the mutant microorganism produced 5-aminolevulinic acid in an amount equivalent to at least 20 times the amount produced by conventional *Corynebacterium glutamicum*.

Therefore, in one aspect, the present invention is directed to a mutant microorganism having the ability to produce 5-aminolevulinic acid wherein a gene encoding mutant glutamyl-tRNA reductase having two lysines added to position 3 of the amino acid sequence thereof is introduced in a glutamic acid-producing microorganism.

In the present invention, HemA genes encoding glutamyl-tRNA reductase were obtained from five kinds of strains, including *Corynebacterium glutamicum*, *E. coli*, *Bacillus subtilis*, *Klebsiella pneumoniae*, and *Salmonella typhimurium* (SEQ ID NOs: 1 to 5).

A mutant strain transformed with the HemA gene derived from *Salmonella typhimurium*, among these genes, showed the highest 5-aminolevulinic acid productivity.

The sequences of the five HemA genes are set forth in SEQ ID NOs: 1 to 5, and amino acid sequences encoded by these gene sequences are set forth in SEQ ID NOs: 6 to 10.

In addition, in order to reduce the effect of heme on the inhibition of enzymatic activity, lysine was introduced into amino acid positions 3 and 4 of each of the HemA genes.

Thus, the glutamyl-tRNA reductase may have two lysines added to position 3 of the amino acid sequence thereof.

In the present invention, the mutant microorganism may be a mutant microorganism wherein a gene encoding glutamate-1-semialdehyde aminotransferase is further introduced in the glutamic acid-producing microorganism.

In an example of the present invention, a glutamate-1-semialdehyde aminotransferase-encoding gene (HemL) from *E. coli* was amplified and introduced into the *Corynebacterium* mutant microorganism, and the promoter region of a pMTls expression vector was replaced with a highly active trc promoter among constitutive promoters, thereby constructing a recombinant vector comprising each enzyme. Using a transformant comprising the recombinant vector, 5-aminolevulinic acid can be efficiently produced in large amounts. The present invention is a cost-effective and efficient technology for the production of 5-aminolevulinic acid that has recently been studied. Furthermore, the present invention is a first study on the production of 5-aminolevulinic acid using *Corynebacterium* and is a very useful invention.

In the present invention, the gene encoding glutamate-1-semialdehyde aminotransferase may be derived from *E. coli*.

In the present invention, the glutamic acid-producing microorganism may be a *Corynebacterium* sp. strain, preferably a *Corynebacterium glutamicum* strain.

In another aspect, the present invention is directed to a method for producing 5-aminolevulinic acid, comprising the steps of: (a) culturing in a glucose-containing medium the above-described mutant microorganism having the ability to produce 5-aminolevulinic acid, thereby producing 5-aminolevulinic acid; and (b) recovering the produced 5-aminolevulinic acid.

In the present invention, in order to increase the production of 5-aminolevulinic acid, either penicillin G that inhibits the activity of 2-oxoglutarate dehydrogenase complex in the cellular metabolic pathway to induce the metabolic pathway to produce glutamic acid or 2,2-dipyridyl that acts as a chelate to reduce the production of heme may be added to the medium of step (a).

In the present invention, penicillin G (6 U/mL) and 2,2'-dipyridyl (250 μM) were added to the medium after 12 hours of culture for production of 5-aminolevulinic acid. Penicillin G inhibits the activity of 2-oxoglutarate dehydrogenase complex in the cellular metabolic pathway to induce the metabolic pathway to produce glutamic acid. In addition, 2,2-dipyridyl acts as a chelate during culture to reduce the production of heme.

In an example of the present invention, 5-aminolevulinic acid was produced by culturing transformed *Corynebacterium glutamicum* with an optimized medium. The recombinant microorganism according to the present invention can stably produce 5-aminolevulinic acid by using a bacterial gene rather than using an eukaryotic gene, and the strain is also a GRAS strain that is advantageous in that it can directly use produced 5-aminolevulinic acid.

The transformant of the present invention may be cultured using a conventional method which is used in culture of hosts. In addition, the culture process may be carried out using any conventional methods for microbial culture, including a batch culture method, a fed-batch culture method, a continuous culture method, and a reactor-type culture method. Examples of a medium for culturing the transformant obtained using bacteria (such as *E. coli*) as a host include complete media or synthetic media, for example, LB medium, NB medium and the like. Also, the transformant is cultured at a suitable temperature, for example, about 30° C., to accumulate ALAS in the microbial cells, and the accumulated ALAS is recovered.

A carbon source is necessary for growth of microorganisms. Examples of carbon sources that can be used in the present invention include: saccharides such as glucose, fructose, sucrose, maltose, galactose and starch; lower alcohols such as ethanol, propanol and butanol; organic acids such as acetic acid, citric acid, succinic acid, tartaric acid, lactic acid and gluconic acid; and fatty acids such as propionic acid, butanoic acid, pentanoic acid, hexanoic acid, heptanoic acid, octanoic acid, nonanoic acid, decanoic acid, undecanoic acid and dodecanoic acid.

Examples of nitrogen sources that can be used in the present invention include naturally-derived products such as peptone, meat juice, yeast extract, malt extract, casein degradation products and corn steep liquor, in addition to ammonium salts such as ammonia, ammonium chloride, ammonium sulfate and ammonium phosphate. In addition, examples of inorganic substances that can be used in the present invention include monobasic potassium phosphate, dibasic potassium phosphate, magnesium phosphate, magnesium sulfate and sodium chloride. Antibiotics such as kanamycin, ampicillin, tetracycline, chloramphenicol and streptomycin may be added to the culture medium.

Also, in the case where an inductive promoter is used in the expression vector, an inductive material corresponding to the promoter may be added to the medium to promote expression when the transformant is cultured. Such inductive materials may include, for example, isopropyl-1-thio-β-D-galactoside (IPTG), tetracycline and indolacrylic acid (IAA).

In still another aspect, the present invention is directed to a method for producing a mutant microorganism having the ability to produce 5-aminolevulinic acid, the method comprising introducing a gene encoding glutamyl-tRNA reductase into a glutamic acid-producing microorganism.

In an example of the present invention, a mutant microorganism was produced by introducing a glutamyl-tRNA reductase-encoding HemA gene into a *Corynebacterium* strain, and a glutamate-1-semialdehyde aminotransferase-encoding gene (HemL) from *E. coli* was amplified and introduced into the mutant microorganism. In addition, the promoter region of a pMTls expression vector was replaced with a highly active trc promoter among constitutive promoters, thereby constructing a recombinant vector comprising each enzyme.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably, as the plasmid is the most commonly used form of vector. For the purpose of the present invention, the plasmid vector is preferably used. A typical plasmid vector which can be used for this purpose contains: (a) a replication origin by which replication occurs efficiently such that several hundred plasmid vectors per host cell are created; (b) an antibiotic-resistant gene by which host cells transformed with the plasmid vector can be selected; and (c) restriction enzyme cutting sites into which foreign DNA fragments can be inserted. Even if suitable restriction enzyme cutting sites are not present in the vector, the use of a conventional synthetic oligonucleotide adaptor or linker enables the easy ligation between the vector and the foreign DNA fragments. After ligation, the vector should be transformed into suitable host cells. The transformation can be easily achieved by the calcium chloride method or electroporation (Neumann, et al., *EMBO J.*, 1:841, 1982).

As the vector which is used for the expression of the gene according to the present invention, an expression vector known in the art may be used.

A nucleotide sequence is operably linked when it is arranged in a functional relationship with another nucleic acid sequence. The nucleotide sequence may be a gene and a control sequence(s) linked to be capable of expressing the gene when a suitable molecule binds to a control sequence(s) (e.g., transcription-activating protein). For example, DNA for a pre-sequence or a secretory leader is operably linked to a DNA encoding a polypeptide when expressed as a pre-protein participating in secretion of the polypeptide; a promoter or an enhancer is operably linked to a coding sequence when affecting the transcription of the sequence; or a ribosome binding site is operably linked to a coding sequence when affecting the transcription of the sequence, or to a coding sequence when arranged to facilitate translation. Generally, the term "operably linked" means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site. However, when this site does not exist, a synthetic oligonucleotide adaptor or a linker is used according to a conventional method.

As is well known in the art, in order to increase the expression level of a transfected gene in a host cell, a corresponding gene should be operably linked to transcription and translation expression control sequences which are operated in a selected expression host. Preferably, the expression control sequences and the corresponding gene are included in one expression vector together with a bacterial selection marker and a replication origin. When an expression host cell is a eukaryotic cell, a recombinant vector should further include an expression marker which is useful in an eukaryotic expression host.

The transformed cell constitutes another aspect of the present invention by the aforementioned expression vector. As used herein, the term "transformation" means that DNA can be replicated as a factor outside of chromosome or by means of completion of the entire chromosome by introducing DNA into a host chromosome.

Of course, it should be understood that all vectors and expression control sequences do not equally function to express DNA sequences according to the present invention. Similarly, all hosts do not equally function with respect to the same expression system. However, one skilled in the art may appropriately select from among various vectors, expression control sequences, and hosts without either departing from the scope of the present invention or bearing excessive experimental burden. For example, a vector must be selected considering a host, because the vector must be replicated in the host. Specifically, the copy number of the vector, the ability of regulating the copy number and the expression of other protein encoded by the corresponding vector (e.g., the expression of an antibiotic marker) should also be considered.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Construction of Recombinant Vector by Promoter Replacement for Gene Overexpression To construct a recombinant vector, the promoter and signal sequence region of pMTls (Hyun, J E et al., *Enzyme Microb. Technol.*, 371-377, 2011) was replaced with trc promoter that is a constitutive promoter. The trc promoter used for replacement was amplified so that a restriction enzyme XhoI recognition sequence would be inserted into the forward promoter and a restriction enzyme BamHI recognition sequence would be inserted into the reverse promoter. Then, the promoter and signal sequence region of pMTls was replaced with the amplified promoter.

The constructed recombinant vector was named "pMT-Trc", and used for expression of each enzyme in the following Examples.

```
pMT-Trc F:
                                    (SEQ ID NO: 11)
AATAGCCTCGAGCGACTGCACGGTGCACCAATG pMT-Trc R:
                                    (SEQ ID NO: 12)
GCATTAGGATCCTTCCTGTGTGAAATTGTTATCCG
```

Example 2: Acquisition of HemA Gene from Five Kinds of Strains and Introduction of the Gene into Recombinant Vector 2-1: Acquisition of HemA Gene from *Corynebacterium glutamicum*

A glutamyl-tRNA reductase-encoding HemA gene derived from a *Corynebacterium glutamicum* strain was cloned in the following manner. With reference to the nucleotide sequence of the gene, two lysines were inserted into the 5' end of the forward primer by introducing the restriction enzyme BamHI and a nucleotide sequence of AAGAAG corresponding to position 7 of the gene sequence, and the sequence of NotI was inserted into the 5' end of the reverse primer, thereby synthesizing primers. Using the synthesized primers, the gene was amplified by PCR. The amplified gene was introduced into the recombinant pMT-Trc vector.

```
HemA-CG F:
                                    (SEQ ID NO: 13)
AATAGCGGATCCCATGGATGATTCAGTACGT

HemA-CG R:
                                    (SEQ ID NO: 14)
GATATAGCGGCCGCATTACTCCCTCGTTTGTGTGGC
```

2-2: Acquisition of HemA Gene from *E. coli*

A glutamyl-tRNA reductase-encoding HemA gene derived from an *E. coli* strain was cloned in the following manner. With reference to the nucleotide sequence of the gene, two lysines were inserted into the 5' end of the forward primer by introducing the restriction enzyme BamHI and a nucleotide sequence of AAGAAG corresponding to position 7 of the gene sequence, and the sequence of NotI was inserted into the 5' end of the reverse primer, thereby synthesizing primers. Using the synthesized primers, the gene was amplified by PCR. The amplified gene was introduced into the recombinant pMT-Trc vector.

```
HemA-EC F:
                                    (SEQ ID NO: 15)
AATAGCGGATCCCATGACCCTTTTAGCACTC

HemA-EC R:
                                   ((SEQ ID NO: 16)
AGATTAGCGGCCGCACTACTCCAGCCCGAGGCT
```

2-3: Acquisition of HemA Gene from *Bacillus subtilis*

A glutamyl-tRNA reductase-encoding HemA gene derived from a *Bacillus subtilis* strain was cloned in the following manner. With reference to the nucleotide sequence of the gene, two lysines were inserted into the 5' end of the forward primer by introducing the restriction enzyme BamHI and a nucleotide sequence of AAGAAG corresponding to position 7 of the gene sequence, and the sequence of NotI was inserted into the 5' end of the reverse primer, thereby synthesizing primers. Using the synthesized primers, the gene was amplified by PCR. The amplified gene was introduced into the recombinant pMT-Trc vector.

```
HemA-BS F:
                                    (SEQ ID NO: 17)
GAATCAGGATCCCATGCATATACTTGTTGTG

HemA-BS R:
                                    (SEQ ID NO: 18)
GCATATGGTACCTCACTCACTTACAAGTGGGCTAAA
```

2-4: Acquisition of HemA Gene from *Salmonella typhimurium*

A glutamyl-tRNA reductase-encoding HemA gene derived from a *Salmonella typhimurium* strain was cloned in the following manner. With reference to the nucleotide sequence of the gene, two lysines were inserted into the 5' end of the forward primer by introducing the restriction enzyme BamHI and a nucleotide sequence of AAGAAG corresponding to position 7 of the gene sequence, and the sequence of NotI was inserted into the 5' end of the reverse primer, thereby synthesizing primers. Using the synthesized primers, the gene was amplified by PCR. The amplified gene was introduced into the recombinant pMT-Trc vector.

```
HemA-ST F:
                                       (SEQ ID NO: 19)
GCAAGGATCCCATGACCCTTTTAGCGCTCGGT

HemA-ST R:
                                       (SEQ ID NO: 20)
GCAATAGGTACCCTACTCCAGCCCGAGGCT
```

2-5: Acquisition of HemA Gene from *Klebsiella pneumoniae*

A glutamyl-tRNA reductase-encoding HemA gene derived from a *Klebsiella pneumoniae* strain was cloned in the following manner. With reference to the nucleotide sequence of the gene, two lysines were inserted into the 5' end of the forward primer by introducing the restriction enzyme BamHI and a nucleotide sequence of AAGAAG corresponding to position 7 of the gene sequence, and the sequence of NotI was inserted into the 5' end of the reverse primer, thereby synthesizing primers. Using the synthesized primers, the gene was amplified by PCR. The amplified gene was introduced into the recombinant pMT-Trc vector.

```
HemA-KP F:
                                       (SEQ ID NO: 21)
AATAGCGGATCCCATGACCCTTTTAGCTCTT

HemA-KP R:
                                       (SEQ ID NO: 22)
ACTATAGCGGCCGCACTATTCCAGCCCGAGGCT
```

Each of the gene amplification products was purified by a PCR purification kit (GeneAll), and digested with the restriction enzymes together with the pMT-Trc vector constructed in Example 1. Each of the DNA fragments was electrophoresed on 0.8% agarose gel, and the DNA fragments on the agarose gel were recovered using a gel extraction kit (GeneAll). Each of the recovered DNA fragments was ligated by T4 ligase, thereby constructing expression vectors.

Figure 2:
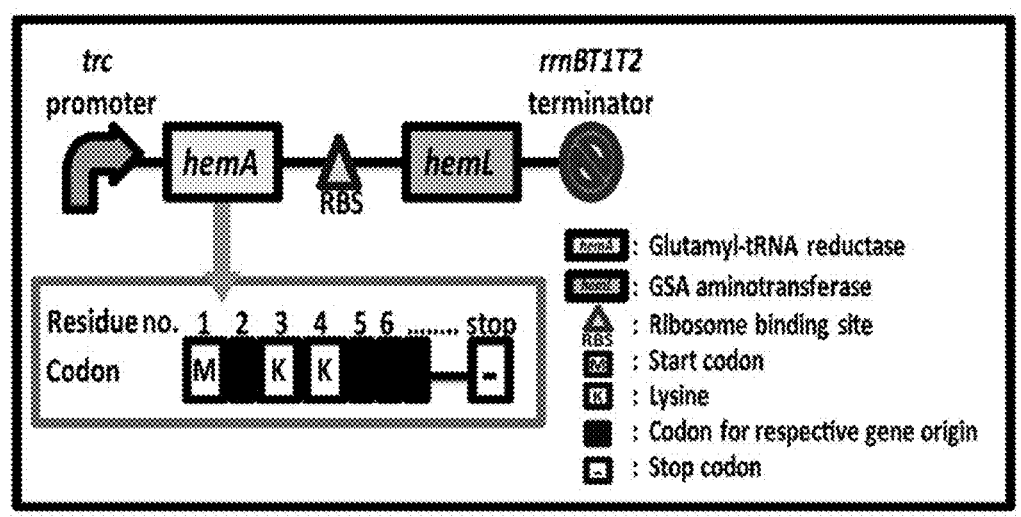
FIG. 2 shows a gene expression cassette for biosynthesis of 5-aminolevulinic acid and a HemA gene having two lysines inserted therein.

Example 3: Comparison of Activities of Five Strain-Derived HemA Genes Having Two Lysines Introduced Therein Lysine was introduced into positions 3 and 4 of the amino acid sequence of each strain gene by a PCR technique (FIG. 2).

```
HemA-CG F:
                                       (SEQ ID NO: 23)
AATAGCGGATCCCATGGATAAGAAGGATTCAGTACGT

HemA-CG R:
                                       (SEQ ID NO: 24)
GATATAGCGGCCGCATTACTCCCTCGTTTGTGTGGC

HemA-EC F:
                                       (SEQ ID NO: 25)
AATAGCGGATCCCATGACCAAGAAGCTTTTAGCACTC

HemA-EC R:
                                       (SEQ ID NO: 26)
AGATTAGCGGCCGCACTACTCCAGCCCGAGGCT

HemA-BS F:
                                       (SEQ ID NO: 27)
GAATCAGGATCCCATGCATAAGAAGATACTTGTTGTG

HemA-BS R:
                                       (SEQ ID NO: 28)
GAATCAGGATCCCATGCATAAGAAGATACTTGTTGTG

HemA-ST F:
                                       (SEQ ID NO: 29)
GCAAGGATCCCATGACCAAGAAGCTTTTAGCGCTCGGT

HemA-ST R:
                                       (SEQ ID NO: 30)
GCAATAGGTACCCTACTCCAGCCCGAGGCT

HemA-KP F:
                                       (SEQ ID NO: 31)
AATAGCGGATCCCATGACCAAGAAGCTTTTAGCTCTT

HemA-KP R:
                                       (SEQ ID NO: 32)
ACTATAGCGGCCGCACTATTCCAGCCCGAGGCT
```

Method for Transformation into *Corynebacterium glutamicum*

1. Culture Medium and Conditions:

MB broth: 10 g tryptone, 5 g NaCl, 4 g yeast extract and g peptone/L. SSBK plate: 40 g BHI, 16 g agar, 40 g sorbitol and 10 g sucrose/1 L kanamycin (25 mg/L). Buffer for electroporation-competent *Corynebacterium*: Hepes 0.5 M (23.8 g/200 ml) stock pH 7.2. EPB 1 (20 mM Hepes pH 7.2, 5% Glycerol), EPB 2 (5 mM Hepes pH 7.2, 15% Glycerol). Recovery medium (4 g BHI, 3 g sorbitol, 1 g sucrose/100 ml. All samples were cultured at 30° C. and 250 rpm.

2. Preparation of Competent Cells for Transformation:

5 ml of a preculture of *Corynebacterium* was prepared, and then 2 ml of the preculture was inoculated into 100 ml of MB broth. The preculture was cultured at 30° C. and 250 rpm until it reached an $OD_{600}$ of about 0.6. 12 ul of ampicillin (12.5 mg/ml) was added to the cells (final concentration of ampicillin: 1.5 µg/ml), followed by incubation for 1-1.5 hours. After centrifugation at 5,000 rpm for 5 minutes, the pellets were suspended in 30 ml of EPB. This process was repeated three times. After centrifugation at 5,000 rpm for 5 minutes, the pellets were suspended in 1.5 ml of EPB 2.

3. Transformation by Electroporation:

150 µl of competent cells were lysed, and about 1-2 µl of DNA was added. For DNA-free cells, an empty vector was added for negative and positive controls. A sample was also added in the same manner. Stored on ice for 5 minutes. Using a Pasteur pipette, the cell/DNA mixture was transferred to a cuvette. The mixture was carefully agitated so that no bubble occurred, and the agitated mixture was pulsed in an *E. coli* pulser. The pulsed mixture was immediately added to a 15-ml tube containing 0.75 ml recovery broth. Then, the mixture was incubated at 30° C. and 250 rpm for 1.5 hours. The incubated mixture was spread on the SSBK plate for selection.

Figure 3:
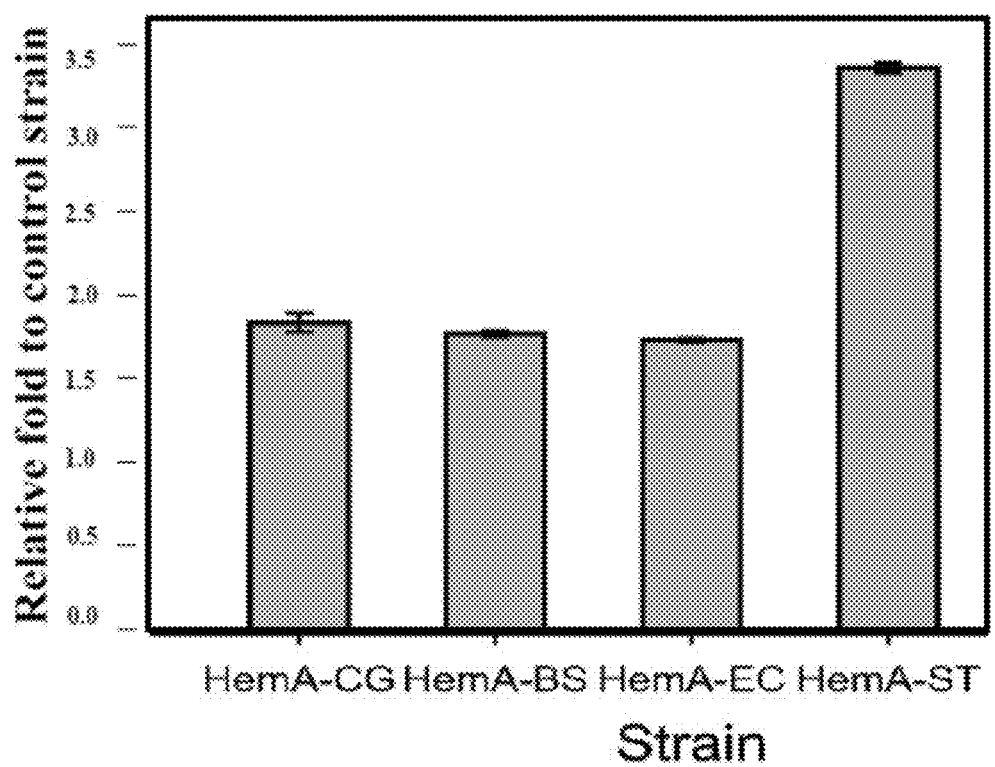
FIG. 3 shows the relative 5-aminolevulinic acid productivity of mutant strains that express the HemA gene (HemA-CG, *C. glutamicum*; HemA-BS, *Bacillus subtilis*; HemA-EC, *E. coli*; HemA-ST, *S. typhimurium*).

To measure the activity of each of the expressed glutamyl-tRNA reductase HemA genes, a change in the production of 5-aminolevulinic acid was measured based on $OD_{600}$ by an UV-Vis spectrophotometer using Ehrlich reagent, and the results of the measurement are shown in FIG. 3. As a result, it was shown that the HemA gene derived from *Salmonella* typhimurium showed the highest activity. In the following Examples, the HemA gene derived from *Salmonella typhimurium* was used.

Example 4: Introduction of Glutamate-1-Semialdehyde Aminotransferase and Synergistic Effect with Glutamyl-tRNA Reductase To clone glutamate-1-semialdehyde aminotransferase (HemL), genomic DNA was extracted from *E. coli* BL21. The nucleotide sequence of the restriction enzyme BamHI was inserted into each of the 5' end of the forward primer and the 5' end of the reverse primer. Using the primers, the gene was amplified.

```
HemLF:
                                             (SEQ ID NO: 33)
GCGGCGGGTACCAAGGAGATATACATGAGTAAGTCTGAAAAT

HemLR:
                                             (SEQ ID NO: 34)
GACTATGGTACCTCACAACTTCGCAAACACCCGACGTGC
```

Figure 4:
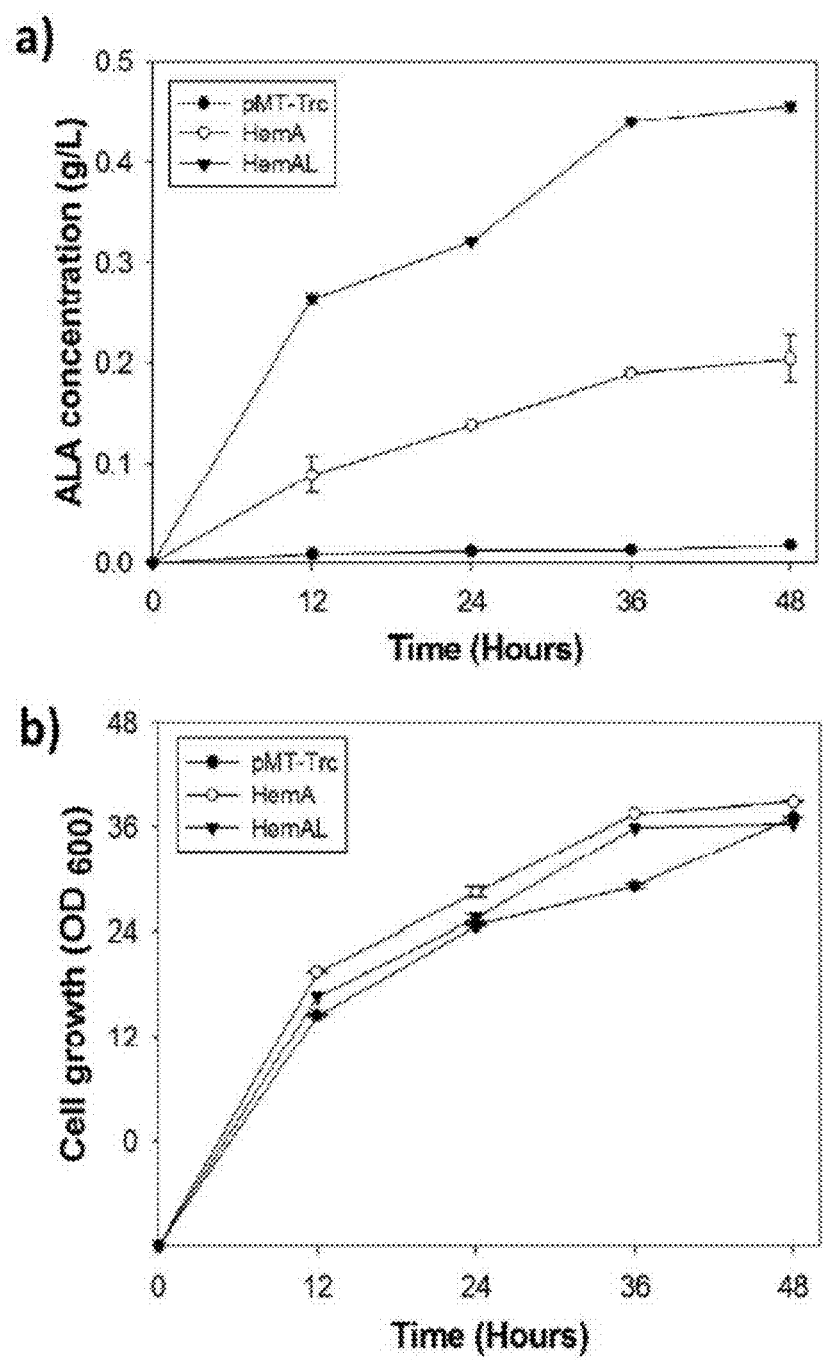
FIG. 4 shows the 5-aminolevulinic acid productivity (a and growth curve (b of *Corynebacterium glutamicum* that overexpresses the HemA gene and the HemL gene.

The amplified gene was introduced into the pMT-trc vector containing the HemA gene and was expressed in *Corynebacterium glutamicum*. As shown in FIG. 4, the expressed HemL gene showed the effect of increasing the production of 5-aminolevulinic acid together with the HemA gene.

Figure 5:
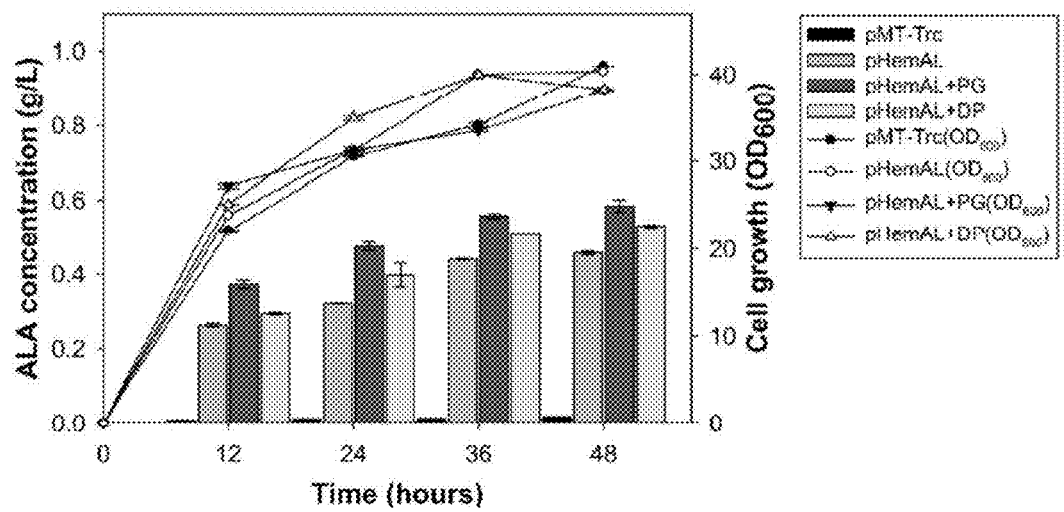
FIG. 5 shows the change in 5-aminolevulinic acid productivity by addition of penicillin G (6 U/mL) (PG) and 2,2-dipyridyl (250 μM) (DP) in a process of producing 5-aminolevulinic acid using a mutant microorganism having the ability to produce 5-aminolevulinic acid.

Example 5: Increase in Flux of Glutamic Acid Production Pathway by Addition of Penicillin G In order to increase the production of 5-aminolevulinic acid, penicillin G (6 U/mL) and 2,2'-dipyridyl (250 µM) were added 12 hours of culture for production of 5-aminolevulinic acid. Penicillin G inhibits the activity of 2-oxoglutarate dehydrogenase complex in the cellular metabolic pathway to induce the metabolic pathway to produce glutamic acid. In addition, 2,2-dipyridyl acts as a chelate during culture to reduce the production of heme. FIG. 5 shows the effect of each of the additives on the production of 5-aminolevulinic acid. As a result, 2,2-dipyridyl increased about 29.9-fold the production of 5-aminolevulinic acid, and penicillin G increased about 33-fold the production of 5-aminolevulinic acid.

Example 6: Examination of Increase in Production of 5-Aminolevulinic Acid by Large-Scale Culture The culture for production of 5-aminolevulinic acid, performed while adding penicillin G, was analyzed using three different recombinant strains which comprise an empty vector, a vector having HemA alone introduced therein, and a vector having both HemA and HemL introduced therein, respectively.

Figure 6:
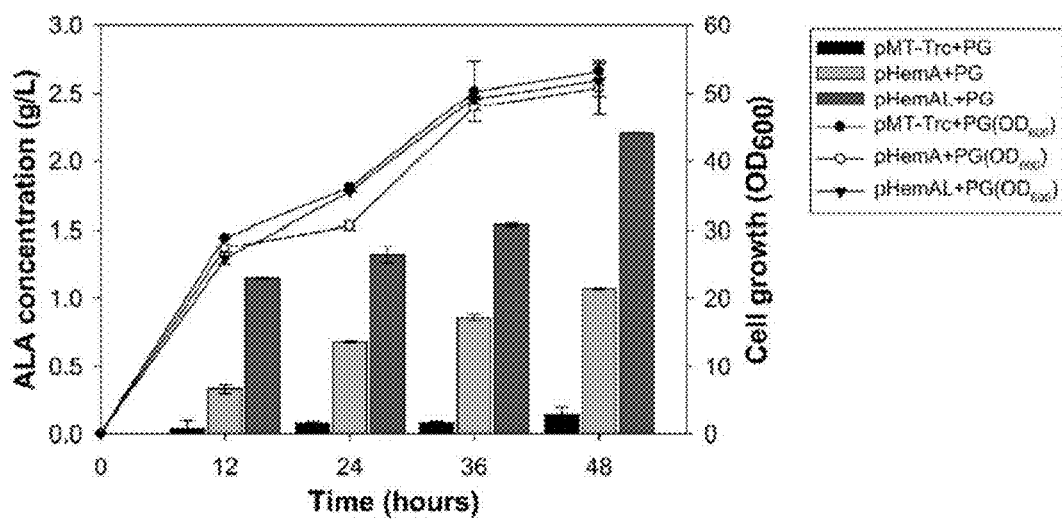
FIG. 6 shows the results of analyzing the 5-aminolevulinic acid production of a *Corynebacterium glutamicum* mutant strain in large-scale fermentation under glutamic acid-enhanced conditions.

As a result, as shown in FIG. 6, the production of 5-aminolevulinic acid in the *Corynebacterium glutamicum* transformant comprising the vector having both HemA and HemL introduced therein was increased up to 22 times that in the control group.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for producing 5-aminolevulinic acid, comprising the steps of:
   (a) culturing in a medium comprising glucose and penicillin G, a mutant microorganism having the ability to produce 5-aminolevulinic acid, wherein the mutant microorganism is a glutamic acid-producing microorganism and is transformed with a gene encoding a mutant glutamyl tRNA reductase, wherein the mutant glutamyl tRNA reductase comprises the amino acid sequence of SEQ ID NO: 6, SEQ ID NO: 7, SEQ ID NO: 8, SEQ ID NO: 9, or SEQ ID NO: 10, except for an insertion of two lysines between residues 2 and 3 of the respective sequence, thereby producing 5-aminolevulinic acid; and
   (b) recovering the produced 5-aminolevulinic acid,
   wherein the mutant microorganism has an increased ability to produce 5-aminolevulinic acid as a result of the presence of the penicillin G in the medium, as compared to production of 5-aminolevulinic acid by the mutant microorganism in a corresponding medium lacking said penicillin G.

2. A method for producing 5-aminolevulinic acid, comprising the steps of:
   (a) culturing in a medium comprising glucose and penicillin G, a mutant microorganism having the ability to produce 5-aminolevulinic acid, wherein the mutant microorganism is a glutamic acid-producing microorganism and is transformed with a gene encoding a mutant glutamyl tRNA reductase, wherein the mutant glutamyl tRNA reductase comprises the amino acid sequence of SEQ ID NO: 6, SEQ ID NO: 7, SEQ ID NO: 8, SEQ ID NO: 9, or SEQ ID NO: 10, except for an insertion of two lysines between residues 2 and 3 of the respective sequence, and wherein the mutant microorganism is further transformed with a gene encoding glutamate-1-semialdehyde aminotransferase, thereby producing 5-aminolevulinic acid; and
   (b) recovering the produced 5-aminolevulinic acid,
   wherein the mutant microorganism has an increased ability to produce 5-aminolevulinic acid as a result of the presence of the penicillin G in the medium, as compared to production of 5-aminolevulinic acid by the mutant microorganism in a corresponding medium lacking said penicillin G.

* * * * *

UNITED STATES PATENT AND TRADEMARK OFFICE
CERTIFICATE OF CORRECTION

PATENT NO. : 10,351,885 B2
APPLICATION NO. : 15/218029
DATED : July 16, 2019
INVENTOR(S) : Sung Ok Han et al.

Page 1 of 1

It is certified that error appears in the above-identified patent and that said Letters Patent is hereby corrected as shown below:

In the Specification

Column 2, Line 34: "hemi" should be -- hemT --.

Signed and Sealed this
Tenth Day of September, 2019

Andrei Iancu
*Director of the United States Patent and Trademark Office*

SEQUENCE LISTING

```
<160> NUMBER OF SEQ ID NOS: 34

<210> SEQ ID NO 1
<211> LENGTH: 1395
<212> TYPE: DNA
<213> ORGANISM: Corynebacterium glutamicum

<400> SEQUENCE: 1
atggtgagtg tactcatcgt agggatgtcg cacaggtctg cgcctgtgtc gcttcttgaa      60
cgtctgagca tggatgattc agtacgtggt gaaacaactc aagcactcct gggtagggcg     120
tctttaagcg aggccctcat tgtctctacg tgtaaccgcc tggaggtcta caccgtcact     180
agcagtttcc atactggtgt taatgatgtg gtggaggttc tccatgaggc aagtggcgta     240
gatattgaaa ctttgcgcgg atatctttat gtccgttacg ccgatgctgc tgctgaacac     300
atgttggtgg tgacttccgg gttggattcc atggtgttgg gtgagcagca gatcattggt     360
caggtgcgca ctgcgtacca agcagctaat gaatatggtt ctgtcggtcc tgctttgcat     420
tcacttaccc agaccgcgct gcataccggc aagcgcgtgc attcggagac tgctattgat     480
gatgctggtg catcgatggt gtctttcgct gtggatcgcg cgttggtgca gatgggtctt     540
gattcggagg cagaagcccc actatctggc aagacagcct tggtgttggg cgctggcgcg     600
atgagttctc ttgcagccac tcaccttggt cgcgctggaa tttccaactt gatcatggcc     660
aaccgcactc tggaacgtgc cgaaaggctt gcggagcatt ccctagaagc cggagttcct     720
gcagaggttg tggaatacga tcagcgagct tccgcctaca atcgcgttga cctggtagtt     780
```

```
tccgccacgg gagcggatga tttcaccgtg aagcctgagg atattccaga aggtgcttcg      840
ttgatgttgg tggatttgtc catgccacga gacatcgatg atgcttgtgc ggatctgccg      900
ggcgttgatt tggtgaacat cgaacgcctg cacaaggcct cccgtgaggg tggatcgggc      960
atggcgccaa gcgaggaaga agctttggcg attgttcggg aagagttgga ttctttcacc     1020
tctgagcagc gcattcgcga tatcgttcca gctgtgtccg cgttgcgcag gcaggccgcg     1080
tcggtgggaa gcgatgaatt ggatcgactc cgccaacgtg cccccgggat ttccgaggtg     1140
gaatgggggg aagtggagaa acagtgaga cgggtcgtcg ataagcttct tcatgaaccc      1200
actgtgcgcg tcaaggaact ggcggcccgg tccggcagca tctcttatga ttcagctctg     1260
caagagctgt tcggtttgga gtcgctggcg agcaccgcag caccggcaac cacgtccgtc     1320
aacgcgtcag aactgccgga tgcgggtatc gtcgcattcg tgaacgcacc ttctgccaca     1380
caaacgaggg agtaa                                                      1395

<210> SEQ ID NO 2
<211> LENGTH: 1257
<212> TYPE: DNA
<213> ORGANISM: Escherichia coli

<400> SEQUENCE: 2 atgaccctt tagcactcgg tatcaaccat aaaacggcac ctgtatcgct gcgagaacgt       60
gtatcgtttt cgccggataa gctcgatcag gcgcttgaca gcctgcttgc gcagccgatg      120
gtgcagggcg gcgtggtgct gtcgacgtgc aaccgcacgg aactttatct tagcgttgaa      180
gagcaggaca acctgcaaga ggcgttaatc cgctggcttt gcgattatca caatcttaat      240
gaagaagatc tgcgtaaaag cctctactgg catcaggata cgacgcggt tagccattta      300 atgcgtgttg ccagcggcct ggattcactg gttctggggg agccgcagat cctcggtcag      360
gttaaaaaag cgtttgccga ttcgcaaaaa ggtcatatga aggccagcga actggaacgc      420
atgttccaga aatctttctc tgtcgcgaaa cgcgttcgca ctgaaacaga tatcggtgcc      480
agcgctgtgt ctgtcgcttt tgcggcttgt acgctggcgc ggcagatctt gaatcgctc      540 tctacggtca cagtgttgct ggtaggcgcg ggcgaaacta tcgagctggt ggcgcgtcat      600
ctgcgcgaac acaaagtaca agatgatt atcgccaacc gcactcgcga acgtgcccaa      660
attctggcag atgaagtcgg cgcggaagtg attgccctga gtgatatcga cgaacgtctg     720
cgcgaagccg atatcatcat cagttccacc gccagccgt taccgattat cgggaaaggc     780
atggtggagc gcgcattaaa aagccgtcgc aaccaaccaa tgctgttggt ggatattgcc      840
gttccgcgcg atgttgagcc ggaagttggc aaactggcga atgcttatct ttatagcgtt      900
gatgatctgc aaagcatcat ttcgcacaac ctggcgcagc gtaaagccgc agcggttgag      960
gcggaaacta ttgtcgctca ggaaaccagc gaatttatgg cgtggctgcg agcacaaagc     1020
gccagcgaaa ccattcgcga gtatcgcagc caggcagagc aagttcgcga tgagttaacc     1080
gccaaagcgt tagcggccct tgagcagggc ggcgacgcgc aagccattat gcaggatctg     1140
gcatggaaac tgactaaccg cttgatccat gcgccaacga aatcacttca acaggccgcc     1200
cgtgacgggg ataacgaacg cctgaatatt ctgcgcgaca gcctcgggct ggagtag        1257

<210> SEQ ID NO 3
<211> LENGTH: 1368
<212> TYPE: DNA
<213> ORGANISM: Bacillus subtilis

<400> SEQUENCE: 3
```

```
atgcatatac ttgttgtggg agtagattat aaatccgccc ctattgagat acgtgaaaaa      60
gtaagttttc agccgaatga gctggcagaa gcaatggtgc agctgaaaga agagaaaagc     120
attcttgaaa acatcattgt ctcaacctgc aaccgcactg aaatttatgc ggtagtcgac     180
cagcttcata ccggccgtta ttatataaaa aagttttag ctgattggtt tcaattaagc      240
aaagaagagc tgtcaccgtt cttaacgttt tatgagagcg atgccgctgt tgagcattta     300
ttccgtgtag cctgcggact tgattctatg gtgattggcg aaacgcagat tctcggacag     360
gtacgcgaca gctttaaaac agctcagcaa gaaaaaacga tcgggactat ttttaatgag     420
ctgtttaagc aggcagttac agtgggcaaa cggactcacg ccgaaacaga cattggctca     480
aatgcggtgt cagtaagcta tgctgcagtt gaacttgcca aaaaaatctt cggaaatctt     540
tcaagcaagc acatattgat tctcggtgcg gaaaaatgg gcgagcttgc tgcggaaaac      600
ctgcacggac agggaatcgg caaggtcact gtcattaacc aacatactt gaaagcgaag      660 gagcttgcag accgttttc aggtgaagcg agaagcttga atcagcttga aagcgcgctt      720
gcggaggctg atattttaat cagttcaacc ggtgcaagtg aatttgtcgt gtccaaagag     780 atgatgaaa acgcgaataa gcttcgcaag ggacgtccgc tgtttatggt cgacattgcc      840
gtgcctagag atcttgatcc ggcgctgaat gatcttgaag gtgttttcct ttatgatatc     900
gacgatctgg aaggcattgt agaagcgaac atgaaagagc gggagaaac agctgaaaaa     960 gttgaactgt taattgaaga aaccattgtg gaatttaaac aatggatgaa tacacttggt    1020
gttgtgcctg ttatttctgc attgcgcgaa aaggcgcttg ccatccagtc agaaacgatg    1080
gacagcattg agcgtaagct gcctcactta agcacaagag agaaaaaact gttgaacaaa    1140
cacaccaaaa gtattattaa ccaaatgctt cgtgatccga ttttaaaggt gaaagagctt    1200
gcggcagatg ctgattctga agaaaagctc gcgttgttta tgcagatttt tgatattgaa    1260
gaagctgcgg gccgtcaaat gatgaaaacc gttgaaagca gccagaaggt ccactctttt    1320
aagaaggctg aatcaaaagc gggctttagc ccacttgtaa gtgagtga                 1368
```

<210> SEQ ID NO 4
<211> LENGTH: 1257
<212> TYPE: DNA
<213> ORGANISM: Klebsiella pneumoniae

<400> SEQUENCE: 4

```
atgaccctt tagctcttgg catcaatcac aaaacagcgc cggtcgacct gcgagaacgt      60
gtgacgtttt cgccggaaac gctcgatcag gcgctggaga gcttgctggc tcagccgatg     120
gtgcagggtg gggtagtgct gtcgacctgc aaccgcacgg aactctatct cagcgtcgaa     180
gagcaggaca atctgcagga agcgctgatc cgctggctgt gcaactatca cggcctcaac     240
gaagaagacc tgcgtaagag cctctactgg caccaggata tgacgccgt cagccatctg     300 atgcgcgtcg ccagcggcct cgattcgctg gtgctgggcg agccgcagat cctcggccag     360
gtgaaaaaag cgtttgctga ttccagccgc ggtcatctta acgtcagcga actggagcgg     420
atgttccaga agtcgttctc ggtggcaaag cgtgtgcgta ccgaaaccga tatcggcgcc     480
agcgccgttt ccgtcgcgtt cgccgcctgt accctgcgc ggcaaatctt tgaatcgctc      540
tccagcgtca ccgtgttact ggtcggcgcc ggtgaaacca tcgaactggt ggcgcgccat    600
cttcgcgaac atcacgtgcg caaaatggtg attgccaacc gcaccgcga acgcgcccag      660 gcgctggcgg acgaagtggg cgccgagctg attgccctca gcgatatcga cgaacggctg     720
```

```
aaagaggccg acattattat cagctccacc gccagcccgc tgccgatcat cggcaaaggc    780
atggtggagc gcgcgcttaa ggcgcggcgt aaccagccga tgctgctggt ggatatcgcc    840
gttccgcgcg atgtcgaacc ggaggtcggc aaactggcca cgcctacct gtacagcgtc    900
gacgatctgc aaaacatcat tcagcacaac ctggcgcagc gtaaggccgc ggcggtgcag    960
gcggaatcga tcgtcgagca ggagaccagc gaatttatgg cctggctgcg cgcgcagagc   1020
gccagcgaga cgattcgcga ataccgttct cagtctgagc aggtccgtga ggagctgacc   1080
gcgaaggcgc tggccgcgct ggagcagggc ggtgatgccc aggaaattat gcaggatctg   1140
gcccgcaagc tgaccaaccg cctgatccac gcgccaacca atctcttca gcaggccgcc   1200
cgtgacgggg acgacgaacg cctgcatatt ctgcgcaaca gcctcgggct ggaatag     1257

<210> SEQ ID NO 5
<211> LENGTH: 1257
<212> TYPE: DNA
<213> ORGANISM: Salmonella typhimurium

<400> SEQUENCE: 5
atgacccttt tagcgctcgg tattaaccat aaaacggcac ctgtatcgct gcgagaacgc     60
gtaacgtttt cgccggacac gcttgatcag gcgctggaca gcctgcttgc gcagccaatg    120
gtgcagggcg gggtcgtgct gtcaacctgt aaccgtacag agctgtatct gagcgtggaa    180
gagcaggata acctgcaaga agcgctgatc cgctggttat gcgattacca taacctgaac    240
gaggacgatc tgcgcaacag tctgtactgg catcaggaca tgacgccgt cagccacctg    300
atgcgcgtcg ccagcggtct ggattcactg gtgctgggcg aaccgcaaat cctcggtcag    360
gtgaaaaaag cgtttgcgga ttcgcaaaaa ggccaccta acgccagcgc gctggagcga    420
atgtttcaga agtcttttc cgtcgctaag cgagtgcgga ctgaaaccga tatcggcgct    480
agcgccgtct ccgtcgcgtt tgccgcctgt acgctcgccc gccaaatctt tgaatcgctc    540
tcgacggtca ccgtactgtt agttggcgcg gcgaaaccat tgaactggt ggcgcgtcac    600
ctgcgcgagc ataaagtaca aaagatgatt atcgccaacc gaacccgcga gcgcgcgcaa    660
gccctggcgg atgaggtagg cgctgaggtt atctcgctca gcgatatcga cgcccgtttg    720
caggatgccg atattattat cagttcgacc gccagcccgc tgccgattat cggtaaaggc    780
atggtggagc gcgcattaaa aagccgtcgc aaccagccga tgctgctggt ggatattgcc    840
gtaccgcgcg acgttgaacc ggaagtcggc aaactggcga cgcttatct ttatagcgtc    900
gatgatttac agagcatcat ttcgcataat ctggcgcagc gtcaggctgc ggcagtagaa    960
gcggaaacga ttgttgagca ggaagccagc gagtttatgg cctggctacg cgcccagggg   1020
gccagcgaga ccattcggga ataccgtagt cagtcggagc agattcgtga cgaactgact   1080
accaaagcgc tgtcggccct tcaacagggc ggtgatgcgc aagccatctt gcaggatctg   1140
gcatggaaac tgaccaaccg cctgattcat gcgccaacga aatcacttca acaggctgcc   1200
cgtgacgggg atgacgaacg cctgaatatt ctgcgcgaca gcctcgggct ggagtag     1257

<210> SEQ ID NO 6
<211> LENGTH: 464
<212> TYPE: PRT
<213> ORGANISM: Corynebacterium glutamicum

<400> SEQUENCE: 6

Met Val Ser Val Leu Ile Val Gly Met Ser His Arg Ser Ala Pro Val
1               5                   10                  15
```

-continued

Ser Leu Leu Glu Arg Leu Ser Met Asp Asp Ser Val Arg Gly Glu Thr
             20                  25                  30

Thr Gln Ala Leu Leu Gly Arg Ala Ser Leu Ser Glu Ala Leu Ile Val
         35                  40                  45

Ser Thr Cys Asn Arg Leu Glu Val Tyr Thr Val Thr Ser Ser Phe His
     50                  55                  60

Thr Gly Val Asn Asp Val Val Glu Val Leu His Ala Ser Gly Val
65                  70                  75                  80

Asp Ile Glu Thr Leu Arg Gly Tyr Leu Tyr Val Arg Tyr Ala Asp Ala
                 85                  90                  95

Ala Ala Glu His Met Leu Val Val Thr Ser Gly Leu Asp Ser Met Val
             100                 105                 110

Leu Gly Glu Gln Gln Ile Ile Gly Gln Val Arg Thr Ala Tyr Gln Ala
         115                 120                 125

Ala Asn Glu Tyr Gly Ser Val Gly Pro Ala Leu His Ser Leu Thr Gln
     130                 135                 140

Thr Ala Leu His Thr Gly Lys Arg Val His Ser Glu Thr Ala Ile Asp
145                 150                 155                 160

Asp Ala Gly Ala Ser Met Val Ser Phe Ala Val Asp Arg Ala Leu Val
                 165                 170                 175

Gln Met Gly Leu Asp Ser Glu Ala Glu Ala Pro Leu Ser Gly Lys Thr
             180                 185                 190

Ala Leu Val Leu Gly Ala Gly Ala Met Ser Ser Leu Ala Ala Thr His
         195                 200                 205

Leu Gly Arg Ala Gly Ile Ser Asn Leu Ile Met Ala Asn Arg Thr Leu
210                 215                 220

Glu Arg Ala Glu Arg Leu Ala Glu His Ser Leu Glu Ala Gly Val Pro
225                 230                 235                 240

Ala Glu Val Val Glu Tyr Asp Gln Arg Ala Ser Ala Tyr Asn Arg Val
                 245                 250                 255

Asp Leu Val Val Ser Ala Thr Gly Ala Asp Asp Phe Thr Val Lys Pro
             260                 265                 270

Glu Asp Ile Pro Glu Gly Ala Ser Leu Met Leu Val Asp Leu Ser Met
         275                 280                 285

Pro Arg Asp Ile Asp Asp Ala Cys Ala Asp Leu Pro Gly Val Asp Leu
     290                 295                 300

Val Asn Ile Glu Arg Leu His Lys Ala Ser Arg Glu Gly Gly Ser Gly
305                 310                 315                 320

Met Ala Pro Ser Glu Glu Glu Ala Leu Ala Ile Val Arg Glu Glu Leu
                 325                 330                 335

Asp Ser Phe Thr Ser Glu Gln Arg Ile Arg Asp Ile Val Pro Ala Val
             340                 345                 350

Ser Ala Leu Arg Arg Gln Ala Ala Ser Val Gly Ser Asp Glu Leu Asp
         355                 360                 365

Arg Leu Arg Gln Arg Ala Pro Gly Ile Ser Glu Val Glu Trp Gly Glu
     370                 375                 380

Val Glu Lys Thr Val Arg Arg Val Val Asp Lys Leu Leu His Glu Pro
385                 390                 395                 400

Thr Val Arg Val Lys Glu Leu Ala Ala Arg Ser Gly Ser Ile Ser Tyr
                 405                 410                 415

Asp Ser Ala Leu Gln Glu Leu Phe Gly Leu Glu Ser Leu Ala Ser Thr
             420                 425                 430

Ala Ala Pro Ala Thr Thr Ser Val Asn Ala Ser Glu Leu Pro Asp Ala

Gly Ile Val Ala Phe Val Asn Ala Pro Ser Ala Thr Gln Thr Arg Glu
    435                 440                 445
450                 455                 460

<210> SEQ ID NO 7
<211> LENGTH: 418
<212> TYPE: PRT
<213> ORGANISM: Escherichia coli

<400> SEQUENCE: 7

Met Thr Leu Leu Ala Leu Gly Ile Asn His Lys Thr Ala Pro Val Ser
1               5                   10                  15

Leu Arg Glu Arg Val Ser Phe Ser Pro Asp Lys Leu Asp Gln Ala Leu
            20                  25                  30

Asp Ser Leu Leu Ala Gln Pro Met Val Gln Gly Gly Val Val Leu Ser
        35                  40                  45

Thr Cys Asn Arg Thr Glu Leu Tyr Leu Ser Val Glu Glu Gln Asp Asn
50                  55                  60

Leu Gln Glu Ala Leu Ile Arg Trp Leu Cys Asp Tyr His Asn Leu Asn
65                  70                  75                  80

Glu Glu Asp Leu Arg Lys Ser Leu Tyr Trp His Gln Asp Asn Asp Ala
            85                  90                  95

Val Ser His Leu Met Arg Val Ala Ser Gly Leu Asp Ser Leu Val Leu
        100                 105                 110

Gly Glu Pro Gln Ile Leu Gly Gln Val Lys Lys Ala Phe Ala Asp Ser
    115                 120                 125

Gln Lys Gly His Met Lys Ala Ser Glu Leu Glu Arg Met Phe Gln Lys
130                 135                 140

Ser Phe Ser Val Ala Lys Arg Val Arg Thr Glu Thr Asp Ile Gly Ala
145                 150                 155                 160

Ser Ala Val Ser Val Ala Phe Ala Ala Cys Thr Leu Ala Arg Gln Ile
            165                 170                 175

Phe Glu Ser Leu Ser Thr Val Thr Val Leu Leu Val Gly Ala Gly Glu
        180                 185                 190

Thr Ile Glu Leu Val Ala Arg His Leu Arg Glu His Lys Val Gln Lys
    195                 200                 205

Met Ile Ile Ala Asn Arg Thr Arg Glu Arg Ala Gln Ile Leu Ala Asp
210                 215                 220

Glu Val Gly Ala Glu Val Ile Ala Leu Ser Asp Ile Asp Glu Arg Leu
225                 230                 235                 240

Arg Glu Ala Asp Ile Ile Ile Ser Ser Thr Ala Ser Pro Leu Pro Ile
            245                 250                 255

Ile Gly Lys Gly Met Val Glu Arg Ala Leu Lys Ser Arg Arg Asn Gln
        260                 265                 270

Pro Met Leu Leu Val Asp Ile Ala Val Pro Arg Asp Val Glu Pro Glu
    275                 280                 285

Val Gly Lys Leu Ala Asn Ala Tyr Leu Tyr Ser Val Asp Asp Leu Gln
290                 295                 300

Ser Ile Ile Ser His Asn Leu Ala Gln Arg Lys Ala Ala Ala Val Glu
305                 310                 315                 320

Ala Glu Thr Ile Val Ala Gln Glu Thr Ser Glu Phe Met Ala Trp Leu
            325                 330                 335

Arg Ala Gln Ser Ala Ser Glu Thr Ile Arg Glu Tyr Arg Ser Gln Ala
        340                 345                 350

```
Glu Gln Val Arg Asp Glu Leu Thr Ala Lys Ala Leu Ala Ala Leu Glu
            355                 360                 365
Gln Gly Gly Asp Ala Gln Ala Ile Met Gln Asp Leu Ala Trp Lys Leu
    370                 375                 380
Thr Asn Arg Leu Ile His Ala Pro Thr Lys Ser Leu Gln Gln Ala Ala
385                 390                 395                 400
Arg Asp Gly Asp Asn Glu Arg Leu Asn Ile Leu Arg Asp Ser Leu Gly
                405                 410                 415
Leu Glu

<210> SEQ ID NO 8
<211> LENGTH: 455
<212> TYPE: PRT
<213> ORGANISM: Bacillus subtilis

<400> SEQUENCE: 8

Met His Ile Leu Val Val Gly Val Asp Tyr Lys Ser Ala Pro Ile Glu
1               5                   10                  15
Ile Arg Glu Lys Val Ser Phe Gln Pro Asn Glu Leu Ala Glu Ala Met
            20                  25                  30
Val Gln Leu Lys Glu Lys Ser Ile Leu Glu Asn Ile Ile Val Ser
        35                  40                  45
Thr Cys Asn Arg Thr Glu Ile Tyr Ala Val Val Asp Gln Leu His Thr
    50                  55                  60
Gly Arg Tyr Tyr Ile Lys Lys Phe Leu Ala Asp Trp Phe Gln Leu Ser
65                  70                  75                  80
Lys Glu Glu Leu Ser Pro Phe Leu Thr Phe Tyr Glu Ser Asp Ala Ala
                85                  90                  95
Val Glu His Leu Phe Arg Val Ala Cys Gly Leu Asp Ser Met Val Ile
            100                 105                 110
Gly Glu Thr Gln Ile Leu Gly Gln Val Arg Asp Ser Phe Lys Thr Ala
        115                 120                 125
Gln Gln Glu Lys Thr Ile Gly Thr Ile Phe Asn Glu Leu Phe Lys Gln
130                 135                 140
Ala Val Thr Val Gly Lys Arg Thr His Ala Glu Thr Asp Ile Gly Ser
145                 150                 155                 160
Asn Ala Val Ser Val Ser Tyr Ala Ala Val Glu Leu Ala Lys Lys Ile
                165                 170                 175
Phe Gly Asn Leu Ser Ser Lys His Ile Leu Ile Leu Gly Ala Gly Lys
            180                 185                 190
Met Gly Glu Leu Ala Ala Glu Asn Leu His Gly Gln Gly Ile Gly Lys
        195                 200                 205
Val Thr Val Ile Asn Arg Thr Tyr Leu Lys Ala Lys Glu Leu Ala Asp
    210                 215                 220
Arg Phe Ser Gly Glu Ala Arg Ser Leu Asn Gln Leu Glu Ser Ala Leu
225                 230                 235                 240
Ala Glu Ala Asp Ile Leu Ile Ser Ser Thr Gly Ala Ser Glu Phe Val
                245                 250                 255
Val Ser Lys Glu Met Met Glu Asn Ala Asn Lys Leu Arg Lys Gly Arg
            260                 265                 270
Pro Leu Phe Met Val Asp Ile Ala Val Pro Arg Asp Leu Asp Pro Ala
        275                 280                 285
Leu Asn Asp Leu Glu Gly Val Phe Leu Tyr Asp Ile Asp Asp Leu Glu
    290                 295                 300
```

```
Gly Ile Val Glu Ala Asn Met Lys Glu Arg Arg Glu Thr Ala Glu Lys
305                 310                 315                 320

Val Glu Leu Leu Ile Glu Glu Thr Ile Val Glu Phe Lys Gln Trp Met
            325                 330                 335

Asn Thr Leu Gly Val Val Pro Val Ile Ser Ala Leu Arg Glu Lys Ala
            340                 345                 350

Leu Ala Ile Gln Ser Glu Thr Met Asp Ser Ile Glu Arg Lys Leu Pro
        355                 360                 365

His Leu Ser Thr Arg Glu Lys Lys Leu Leu Asn Lys His Thr Lys Ser
    370                 375                 380

Ile Ile Asn Gln Met Leu Arg Asp Pro Ile Leu Lys Val Lys Glu Leu
385                 390                 395                 400

Ala Ala Asp Ala Asp Ser Glu Glu Lys Leu Ala Leu Phe Met Gln Ile
            405                 410                 415

Phe Asp Ile Glu Glu Ala Ala Gly Arg Gln Met Met Lys Thr Val Glu
        420                 425                 430

Ser Ser Gln Lys Val His Ser Phe Lys Lys Ala Glu Ser Lys Ala Gly
    435                 440                 445

Phe Ser Pro Leu Val Ser Glu
450                 455

<210> SEQ ID NO 9
<211> LENGTH: 418
<212> TYPE: PRT
<213> ORGANISM: Klebsiella pneumoniae

<400> SEQUENCE: 9

Met Thr Leu Leu Ala Leu Gly Ile Asn His Lys Thr Ala Pro Val Asp
1               5                   10                  15

Leu Arg Glu Arg Val Thr Phe Ser Pro Glu Thr Leu Asp Gln Ala Leu
            20                  25                  30

Glu Ser Leu Leu Ala Gln Pro Met Val Gln Gly Gly Val Val Leu Ser
        35                  40                  45

Thr Cys Asn Arg Thr Glu Leu Tyr Leu Ser Val Glu Glu Gln Asp Asn
    50                  55                  60

Leu Gln Glu Ala Leu Ile Arg Trp Leu Cys Asn Tyr His Gly Leu Asn
65                  70                  75                  80

Glu Glu Asp Leu Arg Lys Ser Leu Tyr Trp His Gln Asp Asn Asp Ala
            85                  90                  95

Val Ser His Leu Met Arg Val Ala Ser Gly Leu Asp Ser Leu Val Leu
        100                 105                 110

Gly Glu Pro Gln Ile Leu Gly Gln Val Lys Lys Ala Phe Ala Asp Ser
    115                 120                 125

Ser Arg Gly His Leu Asn Val Ser Glu Leu Glu Arg Met Phe Gln Lys
130                 135                 140

Ser Phe Ser Val Ala Lys Arg Val Arg Thr Glu Thr Asp Ile Gly Ala
145                 150                 155                 160

Ser Ala Val Ser Val Ala Phe Ala Ala Cys Thr Leu Ala Arg Gln Ile
            165                 170                 175

Phe Glu Ser Leu Ser Ser Val Thr Val Leu Leu Val Gly Ala Gly Glu
        180                 185                 190

Thr Ile Glu Leu Val Ala Arg His Leu Arg Glu His His Val Arg Lys
    195                 200                 205

Met Val Ile Ala Asn Arg Thr Arg Glu Arg Ala Gln Ala Leu Ala Asp
210                 215                 220
```

Glu Val Gly Ala Glu Val Ile Ala Leu Ser Asp Ile Asp Glu Arg Leu
225                 230                 235                 240

Lys Glu Ala Asp Ile Ile Ser Ser Thr Ala Ser Pro Leu Pro Ile
            245                 250                 255

Ile Gly Lys Gly Met Val Glu Arg Ala Leu Lys Ala Arg Arg Asn Gln
            260                 265                 270

Pro Met Leu Leu Val Asp Ile Ala Val Pro Arg Asp Val Glu Pro Glu
            275                 280                 285

Val Gly Lys Leu Ala Asn Ala Tyr Leu Tyr Ser Val Asp Asp Leu Gln
            290                 295                 300

Asn Ile Ile Gln His Asn Leu Ala Gln Arg Lys Ala Ala Ala Val Gln
305                 310                 315                 320

Ala Glu Ser Ile Val Glu Gln Glu Thr Ser Glu Phe Met Ala Trp Leu
                325                 330                 335

Arg Ala Gln Ser Ala Ser Glu Thr Ile Arg Glu Tyr Arg Ser Gln Ser
                340                 345                 350

Glu Gln Val Arg Glu Glu Leu Thr Ala Lys Ala Leu Ala Ala Leu Glu
            355                 360                 365

Gln Gly Gly Asp Ala Gln Glu Ile Met Gln Asp Leu Ala Arg Lys Leu
370                 375                 380

Thr Asn Arg Leu Ile His Ala Pro Thr Lys Ser Leu Gln Gln Ala Ala
385                 390                 395                 400

Arg Asp Gly Asp Asp Glu Arg Leu His Ile Leu Arg Asn Ser Leu Gly
                405                 410                 415

Leu Glu

<210> SEQ ID NO 10
<211> LENGTH: 418
<212> TYPE: PRT
<213> ORGANISM: Salmonella typhimurium

<400> SEQUENCE: 10

Met Thr Leu Leu Ala Leu Gly Ile Asn His Lys Thr Ala Pro Val Ser
1               5                   10                  15

Leu Arg Glu Arg Val Thr Phe Ser Pro Asp Thr Leu Asp Gln Ala Leu
                20                  25                  30

Asp Ser Leu Leu Ala Gln Pro Met Val Gln Gly Gly Val Val Leu Ser
            35                  40                  45

Thr Cys Asn Arg Thr Glu Leu Tyr Leu Ser Val Glu Glu Gln Asp Asn
        50                  55                  60

Leu Gln Glu Ala Leu Ile Arg Trp Leu Cys Asp Tyr His Asn Leu Asn
65                  70                  75                  80

Glu Asp Asp Leu Arg Asn Ser Leu Tyr Trp His Gln Asp Asn Asp Ala
                85                  90                  95

Val Ser His Leu Met Arg Val Ala Ser Gly Leu Asp Ser Leu Val Leu
            100                 105                 110

Gly Glu Pro Gln Ile Leu Gly Gln Val Lys Lys Ala Phe Ala Asp Ser
        115                 120                 125

Gln Lys Gly His Leu Asn Ala Ser Ala Leu Glu Arg Met Phe Gln Lys
    130                 135                 140

Ser Phe Ser Val Ala Lys Arg Val Arg Thr Glu Thr Asp Ile Gly Ala
145                 150                 155                 160

Ser Ala Val Ser Val Ala Phe Ala Ala Cys Thr Leu Ala Arg Gln Ile
                165                 170                 175

```
Phe Glu Ser Leu Ser Thr Val Thr Val Leu Val Gly Ala Gly Glu
            180                 185                 190

Thr Ile Glu Leu Val Ala Arg His Leu Arg Glu His Lys Val Gln Lys
        195                 200                 205

Met Ile Ile Ala Asn Arg Thr Arg Glu Arg Ala Gln Ala Leu Ala Asp
210                 215                 220

Glu Val Gly Ala Glu Val Ile Ser Leu Ser Asp Ile Asp Ala Arg Leu
225                 230                 235                 240

Gln Asp Ala Asp Ile Ile Ser Ser Thr Ala Ser Pro Leu Pro Ile
                245                 250                 255

Ile Gly Lys Gly Met Val Glu Arg Ala Leu Lys Ser Arg Arg Asn Gln
            260                 265                 270

Pro Met Leu Leu Val Asp Ile Ala Val Pro Arg Asp Val Glu Pro Glu
        275                 280                 285

Val Gly Lys Leu Ala Asn Ala Tyr Leu Tyr Ser Val Asp Asp Leu Gln
        290                 295                 300

Ser Ile Ile Ser His Asn Leu Ala Gln Arg Gln Ala Ala Val Glu
305                 310                 315                 320

Ala Glu Thr Ile Val Glu Gln Glu Ala Ser Glu Phe Met Ala Trp Leu
            325                 330                 335

Arg Ala Gln Gly Ala Ser Glu Thr Ile Arg Glu Tyr Arg Ser Gln Ser
            340                 345                 350

Glu Gln Ile Arg Asp Glu Leu Thr Thr Lys Ala Leu Ser Ala Leu Gln
        355                 360                 365

Gln Gly Gly Asp Ala Gln Ala Ile Leu Gln Asp Leu Ala Trp Lys Leu
        370                 375                 380

Thr Asn Arg Leu Ile His Ala Pro Thr Lys Ser Leu Gln Gln Ala Ala
385                 390                 395                 400

Arg Asp Gly Asp Asp Glu Arg Leu Asn Ile Leu Arg Asp Ser Leu Gly
                405                 410                 415

Leu Glu

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
aatagcctcg agcgactgca cggtgcacca atg                              33

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
gcattaggat ccttcctgtg tgaaattgtt atccg                            35

<210> SEQ ID NO 13
<211> LENGTH: 31
<212> TYPE: DNA
<213> ORGANISM: Artificial Sequence
<220> FEATURE:
<223> OTHER INFORMATION: primer
```

<400> SEQUENCE: 13
aatagcggat cccatggatg attcagtacg t                                31

<210> SEQ ID NO 14
<211> LENGTH: 36
<212> TYPE: DNA
<213> ORGANISM: Artificial Sequence
<220> FEATURE:
<223> OTHER INFORMATION: primer

<400> SEQUENCE: 14
gatatagcgg ccgcattact ccctcgtttg tgtggc                           36

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
aatagcggat cccatgaccc ttttagcact c                                31

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16
agattagcgg ccgcactact ccagcccgag gct                              33

<210> SEQ ID NO 17
<211> LENGTH: 31
<212> TYPE: DNA
<213> ORGANISM: Artificial Sequence
<220> FEATURE:
<223> OTHER INFORMATION: primer

<400> SEQUENCE: 17
gaatcaggat cccatgcata tacttgttgt g                                31

<210> SEQ ID NO 18
<211> LENGTH: 36
<212> TYPE: DNA
<213> ORGANISM: Artificial Sequence
<220> FEATURE:
<223> OTHER INFORMATION: primer

<400> SEQUENCE: 18
gcatatggta cctcactcac ttacaagtgg gctaaa                           36

<210> SEQ ID NO 19
<211> LENGTH: 32
<212> TYPE: DNA
<213> ORGANISM: Artificial Sequence
<220> FEATURE:
<223> OTHER INFORMATION: primer

<400> SEQUENCE: 19
gcaaggatcc catgaccctt ttagcgctcg gt                               32

<210> SEQ ID NO 20

```
<211> LENGTH: 30
<212> TYPE: DNA
<213> ORGANISM: Artificial Sequence
<220> FEATURE:
<223> OTHER INFORMATION: primer

<400> SEQUENCE: 20
gcaataggta ccctactcca gcccgaggct                                          30

<210> SEQ ID NO 21
<211> LENGTH: 31
<212> TYPE: DNA
<213> ORGANISM: Artificial Sequence
<220> FEATURE:
<223> OTHER INFORMATION: primer

<400> SEQUENCE: 21
aatagcggat cccatgaccc ttttagctct t                                        31

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
actatagcgg ccgcactatt ccagcccgag gct                                      33

<210> SEQ ID NO 23
<211> LENGTH: 37
<212> TYPE: DNA
<213> ORGANISM: Artificial Sequence
<220> FEATURE:
<223> OTHER INFORMATION: primer

<400> SEQUENCE: 23
aatagcggat cccatggata agaaggattc agtacgt                                  37

<210> SEQ ID NO 24
<211> LENGTH: 36
<212> TYPE: DNA
<213> ORGANISM: Artificial Sequence
<220> FEATURE:
<223> OTHER INFORMATION: primer

<400> SEQUENCE: 24
gatatagcgg ccgcattact ccctcgtttg tgtggc                                   36

<210> SEQ ID NO 25
<211> LENGTH: 37
<212> TYPE: DNA
<213> ORGANISM: Artificial Sequence
<220> FEATURE:
<223> OTHER INFORMATION: primer

<400> SEQUENCE: 25
aatagcggat cccatgacca agaagctttt agcactc                                  37

<210> SEQ ID NO 26
<211> LENGTH: 33
<212> TYPE: DNA
<213> ORGANISM: Artificial Sequence
<220> FEATURE:
<223> OTHER INFORMATION: primer

<400> SEQUENCE: 26
```

-continued agattagcgg ccgcactact ccagcccgag gct                                33

<210> SEQ ID NO 27
<211> LENGTH: 37
<212> TYPE: DNA
<213> ORGANISM: Artificial Sequence
<220> FEATURE:
<223> OTHER INFORMATION: primer

<400> SEQUENCE: 27
gaatcaggat cccatgcata agaagatact tgttgtg                            37

<210> SEQ ID NO 28
<211> LENGTH: 37
<212> TYPE: DNA
<213> ORGANISM: Artificial Sequence
<220> FEATURE:
<223> OTHER INFORMATION: primer

<400> SEQUENCE: 28
gaatcaggat cccatgcata agaagatact tgttgtg                            37

<210> SEQ ID NO 29
<211> LENGTH: 38
<212> TYPE: DNA
<213> ORGANISM: Artificial Sequence
<220> FEATURE:
<223> OTHER INFORMATION: primer

<400> SEQUENCE: 29
gcaaggatcc catgaccaag aagcttttag cgctcggt                           38

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
gcaataggta ccctactcca gcccgaggct                                    30

<210> SEQ ID NO 31
<211> LENGTH: 37
<212> TYPE: DNA
<213> ORGANISM: Artificial Sequence
<220> FEATURE:
<223> OTHER INFORMATION: primer

<400> SEQUENCE: 31
aatagcggat cccatgacca agaagctttt agctctt                            37

<210> SEQ ID NO 32
<211> LENGTH: 33
<212> TYPE: DNA
<213> ORGANISM: Artificial Sequence
<220> FEATURE:
<223> OTHER INFORMATION: primer

<400> SEQUENCE: 32
actatagcgg ccgcactatt ccagcccgag gct                                33

<210> SEQ ID NO 33
<211> LENGTH: 42
<212> TYPE: DNA

```
<213> ORGANISM: Artificial Sequence
<220> FEATURE:
<223> OTHER INFORMATION: primer

<400> SEQUENCE: 33
gcggcgggta ccaaggagat atacatgagt aagtctgaaa at            42

<210> SEQ ID NO 34
<211> LENGTH: 39
<212> TYPE: DNA
<213> ORGANISM: Artificial Sequence
<220> FEATURE:
<223> OTHER INFORMATION: primer

<400> SEQUENCE: 34
gactatggta cctcacaact tcgcaaacac ccgacgtgc                39
```